United States Patent [19]

Sklar et al.

[11] Patent Number: 5,157,428
[45] Date of Patent: Oct. 20, 1992

[54] SPECTRAL DIVISION OF REFLECTED LIGHT IN COMPLEX OPTICAL DIAGNOSTIC AND THERAPEUTIC SYSTEMS

[75] Inventors: H. Alfred Sklar, San Francisco; Alan M. Frank, Livermore, both of Calif.

[73] Assignee: Phoenix Laser Systems, Inc., San Francisco, Calif.

[21] Appl. No.: 719,924

[22] Filed: Jun. 24, 1991

Related U.S. Application Data

[63] Continuation of Ser. No. 523,799, May 15, 1990, Pat. No. 5,048,946.

[51] Int. Cl.$^5$ ............................................. A61B 3/14
[52] U.S. Cl. .................................. 351/206; 351/221; 351/246
[58] Field of Search ............... 350/171, 173; 351/205, 351/206, 221, 243, 246; 128/633, 745; 606/4; 354/62

[56] References Cited

U.S. PATENT DOCUMENTS 3,403,262  9/1968  Seidel .
3,895,854  7/1975  Ziffer .
4,875,761  10/1989  Fetzer .
5,048,946  9/1991  Sklar et al. ........................... 351/221

Primary Examiner—Rodney B. Bovernick
Assistant Examiner—J. P. Ryan
Attorney, Agent, or Firm—Thomas M. Freiburger

[57] ABSTRACT

A diagnostic system for support of laser ocular surgery for example, solves a problem of competition for light which is often encountered when a series of different detectors are used to receive and detect features of a target reflecting an illuminating light beam. The intensity of an illuminating beam, particularly in eye surgery, is limited to a level above which damage to the eye can occur. In a system wherein a plurality of successive beam splitters are used, each reflecting a portion of the light intensity and transmitting the remaining light intensity, the series of detecting devices compete for adequate light intensity for the particular functions being served. The system of the invention solves this problem and increases the effective quantity of light useful from a given input intensity by dividing the light spectrally after its reflection from the eye, thereby making use of a different spectral range of the light at each of the plurality of different detecting devices.

3 Claims, 2 Drawing Sheets

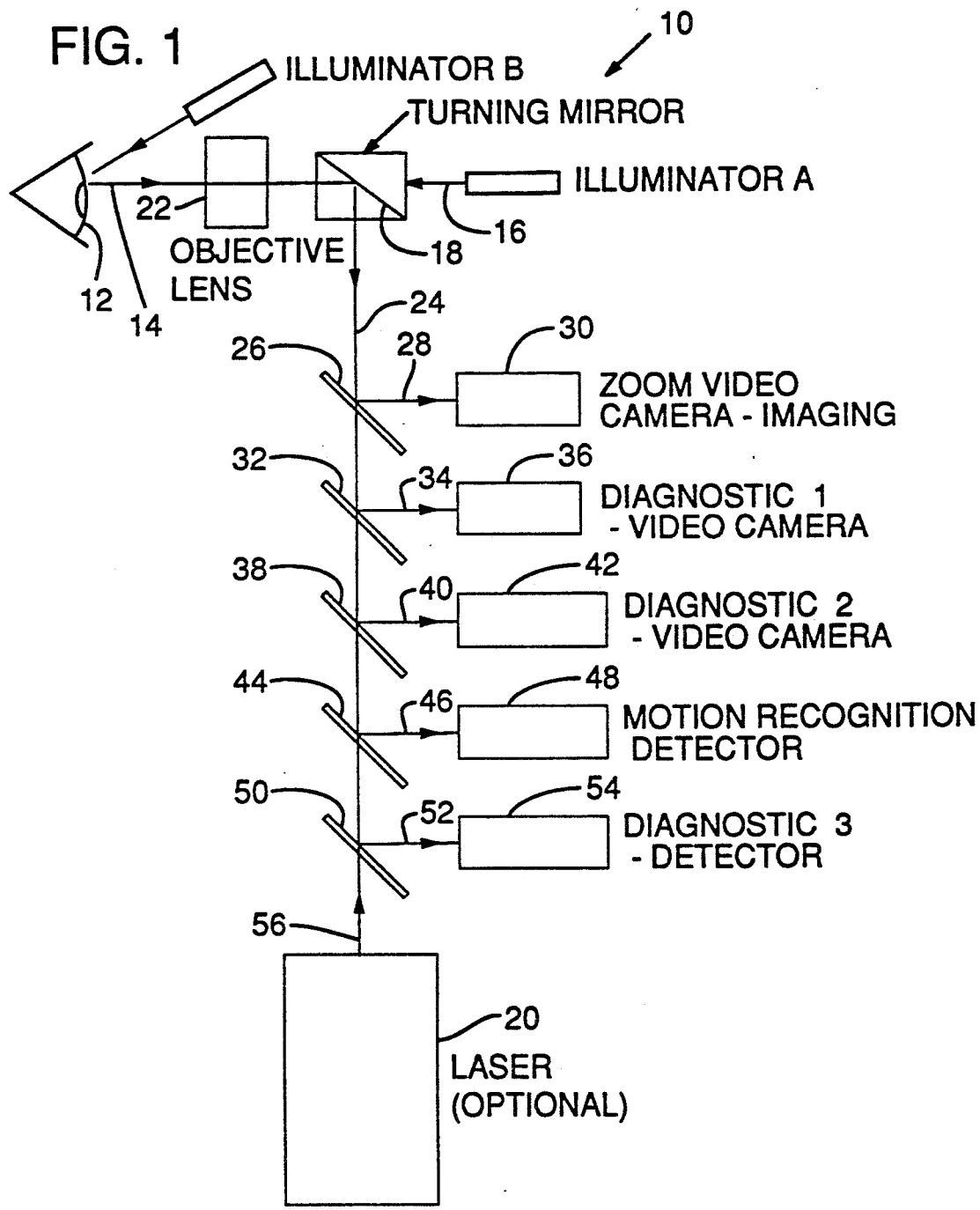

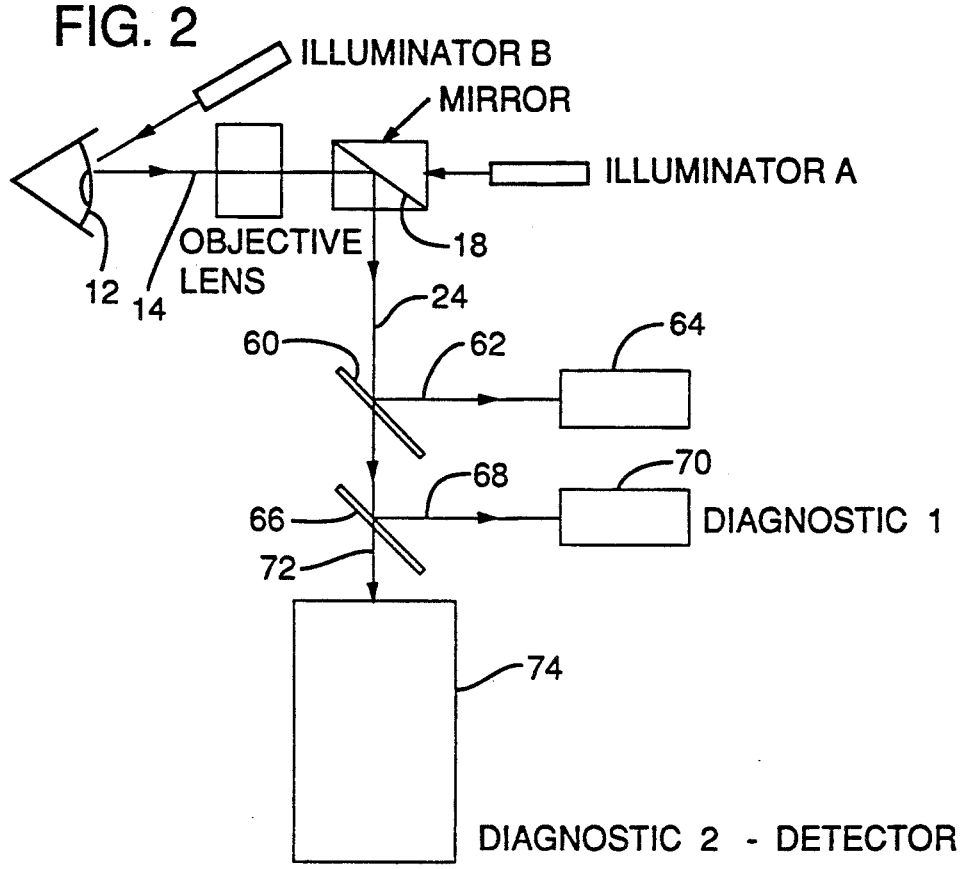
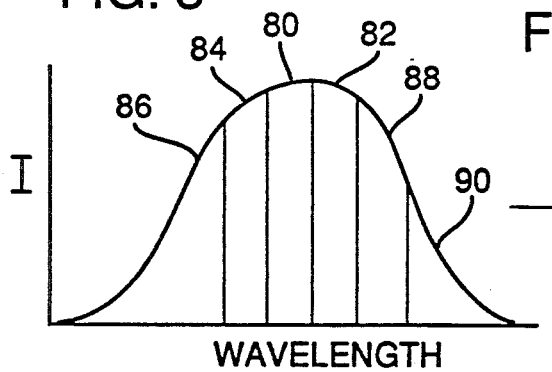
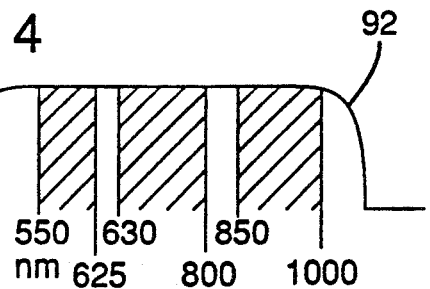

SPECTRAL DIVISION OF REFLECTED LIGHT IN COMPLEX OPTICAL DIAGNOSTIC AND THERAPEUTIC SYSTEMS

This is a continuation of co-pending application Ser. No. 523,799 filed on May 15, 1990 now U.S. Pat. No. 5,048,946.

BACKGROUND OF THE INVENTION

The invention relates to optics, and in particular the invention is concerned with optics for medical applications, as in optical detecting, diagnostic and therapeutic devices The method and apparatus of the present invention are concerned with how a variety of multi-function optical components, all of which would normally be competing for the same reflected signals from a targeted object, can be made to operate simultaneously without significant degradation in performance from any of the component functions and without greatly increasing the required illumination levels Examples of the variety of optical components considered are lasers, multiple real-time diagnostics, on-line video imaging, and other test and measurement equipment.

The history of lasers in medicine now spans nearly three decades Initially, lasers constituted a new technology for medicine, and over the course of the decades an appreciation has developed for the variety of uses which a laser can serve as a therapeutic instrument. As confidence in the viability of lasers to perform therapeutic procedures has grown, new ways of using lasers are continually being studied in an effort to render them more efficacious for an ever increasing range of procedures.

In optical diagnostic equipment for medical purposes, particularly in ophthalmology and ophthalmic surgery, a number of different types of analysis and diagnosis, including topographical and shape imaging, cell counting, video microscope imaging and motion recognition, can be accomplished by directing rays of light reflected from target surfaces onto appropriate forms of detectors.

It may sometimes be desirable to perform a series of different diagnostic and therapeutic functions using coaxial illumination, a common beam of reflected light, such as in ophthalmic diagnosis or in support of ophthalmic surgery. Particularly in ophthalmic practice, it may sometimes be necessary or desirable to split a common reflected beam into a series of beams, such as for topographic imaging, for producing one or more video images, for detection of motion and other functions. In this regard, see U.S. Pat. Nos. 5,098,426 and 5,054,091 filed Feb. 6, 1989 and Dec. 22, 1989, respectively, assigned to the same assignee as the present invention and incorporated by reference herein. The copending applications disclose imaging, tracking and corneal surface detecting equipment. Thus, increasing the effectiveness of laser procedures often requires the coaxial use of optical diagnostic imaging and sensing techniques to better identify the shape and location of individual targets. This can lead to competition for reflected light from the various diagnostic detectors desired. An example of this arises in ophthalmology whenever accurate refractive cataract or vitreo-retinal surgery calls for the on-line integration of a wide array of measurement devices, as indicated to some extent in the systems of the referenced patents In refractive surgery, the surgeon needs to know the initial shape of the cornea, the state of health of said cornea, and an indication of the shape of lesion which will lead to a desired ending shape for said cornea. Moreover, the surgeon needs to be able to establish where the laser lesion is to be positioned and to effect that lesion irrespective of patient eye motions. Furthermore, the surgeon needs to monitor the course of the procedure through some form of direct or indirect imaging.

The usual approach is to use white light illumination, at times polarized, at times subject to UV and IR filters, and essentially white light detectors for each and every different diagnostic element detector required. If only a small number of detectors are needed, this does not place an undue burden on available illumination levels. As more detectors are required, the standard approach is to increase the amount of illumination impingent on the eye to provide sufficient reflected radiance for detection. Another way often used in tandem is to use ever increasingly more sensitive detectors.

There are limitations to both the sensitivity of detectors and to the amount of illumination that a human eye can tolerate without eye damage, let alone discomfort. Also, lenses and reflectors and coatings on these optical elements have practical limits as to the intensity of light and heat that can be withstood without damage.

The spectrum of a typical white light source such as used for surgical illumination or ophthalmic diagnostic illumination purposes generally exhibits a Gaussian distribution. The intensity of the visible spectral portion of the white light is the greatest, with the mid-wavelengths at the peak of the curve. Intensity falls off sharply toward the infrared and ultraviolet ends of the spectrum.

It is known that optical coatings on the surfaces of lenses and mirrors can effect a spectral division of light impinging on the optical element. Such coatings have commonly been used on sunglasses and in various laser applications, causing selected portions of the spectrum, i.e. selected wavelength ranges of light, to be reflected and the remainder to be transmitted.

However, previous to the present invention spectral selectivity via optical coatings on beam splitters and similar optical elements has not been applied in the manner of the present invention described below, for enhancing the utility of a given light intensity for serving multiple diagnostic and imaging functions. In accordance with the invention relatively inexpensive detectors can be used in tandem working off of relatively similar levels of illumination.

SUMMARY OF THE INVENTION

The method, apparatus and system of the present invention solve these problems by increasing the effective quantity of light useful from a given input illumination intensity, by dividing the reflected light spectrally. A different spectral range of the reflected light is used at each of a plurality of different detecting devices, each of which is selected for its sensitivity to the particular spectral range available.

The method and system are particularly useful in optical diagnostics, for enabling the use of a limited-intensity illumination beam to reflect light for a series of different analytical and diagnostic purposes A series of coated beam splitters in the path of the reflected light are used to spectrally divide the returning reflected light beam into different spectral components, each of which is separately reflected out of the coaxial light path for a different diagnostic purpose.

As a consequence, an illuminating beam of relatively low intensity can be used more efficiently to produce information at a number of different detectors, even four or five or six different detectors.

With the system and method of the invention, illumination of the eye can be kept to a safe, relatively low level, while still enabling a considerable number of sensors, viewing and analysis devices to be served by different spectral components of the light source.

In one embodiment of the invention, the illuminating light beam has spectral components in the upper and lower wavelength ranges expanded in intensity while still within safe levels, making the spectral distribution non-Gaussian and more flat. With such modification of the light beam, the uses of the light are even further expanded.

The principles of the present invention are also applicable to other optical diagnostic systems such as in industrial processes, not involving analysis of the eye. In particular, the system is applicable to any process wherein maximum permissible light level is quite limited, and wherein a number of different types of analysis or sensing must be done with the same reflected beam to improve the process, so that there is competition for available light intensity. This could be, for example, where an object of investigation or of an industrial operation can only withstand a limited degree of heat, or where the object is a photosensitive material with a strict limitation on light level.

In one embodiment of the present invention, an optical diagnostic system for ocular analysis includes a plurality of sensors receiving reflected light from a patient's eye for diagnostic purposes. The system includes an illumination means for sending toward the eye an illuminating light beam, which may be delivered axially through an optical path of the system, but which could be delivered off-axis. In the path of reflected light from the eye is at least one beam splitter, positioned so as to receive light from the illuminating beam as reflected from optical surfaces of the eye and back toward the one beam splitter.

A first coating means on at least the first beam splitter in the path of reflected light is provided for reflecting off the path substantially all light within a first preselected wavelength range. The first beam splitter has means for transmitting substantially all of the remaining wavelengths of the reflected light.

A plurality of detecting optical devices are each positioned to receive a portion of the reflected light from the eye, as divided by at least the one beam splitter in the plurality of successive beam splitters. By this arrangement, a substantially greater portion of the spectrum of light in the reflected light from the eye is used for diagnostic purposes on the detecting equipment than would otherwise be available. This enables the intensity of the illuminating light beam to be minimized.

In preferred embodiments there are further successive beam splitters in the path of reflected light from the eye, downstream along the path from the one beam splitter. Coatings are included on successive beam splitters, for reflecting out respective separate spectral portions of the light, and for transmitting the remainder.

It is therefore among the objects of the present invention to provide an improved coaxial optical diagnostic system, wherein a relatively low light level is used to illuminate a patient's eye or another sensitive object or workpiece, with substantially all spectral portions of the light used efficiently for detection and analytical purposes. These and other objects, advantages and features of the invention will be apparent from the following description of a preferred embodiment, considered along with the accompanying claims.

DESCRIPTION OF THE DRAWINGS

FIG. 1 is a schematic diagram showing an arrangement according to the present invention in an optical diagnostic system.

FIG. 2 is a similar view, showing a somewhat modified arrangement, also within the principles of the invention.

FIG. 3 is a graphic representation showing a Gaussian distribution of typical white light, in a plotting of intensity versus wavelength.

FIG. 4 is a graphical representation similar to FIG. 3, but showing an enhanced distribution for light which can be used in accordance with the present invention.

DESCRIPTION OF PREFERRED EMBODIMENTS

In the drawings, FIG. 1 shows an optical diagnostic and/or surgical system 10 in accordance with the principles of the invention. Although the system 10 is illustrated in connection with ophthalmic uses, it should be understood that the system is applicable to any process wherein a maximum permissable illumination level is limited, and wherein a number of different types of analysis or sensing are to be accomplished using the same reflected beam from a workpiece. This can include industrial operations wherein a workpiece or object of investigation can withstand only a limited degree of heat or light but where a multiplicity of different diagnostics of the workpiece are required or desirable.

As shown in FIG. 1, the system 10 of the invention may be used for diagnostics and analysis of a patient's eye 12. The eye may be illuminated by an illuminator B as shown, off-axis and obliquely aimed at the eye; or it may be illuminated by an illuminator A as shown alternatively in FIG. 1. The illuminator A is directly on the axis 14 of returning reflected light from the eye. The axis 14 is not necessarily coincident with the visual axis (not shown) of the eye.

As shown in the illustrative embodiment of FIG. 1, if the illuminator A is used the illuminating beam 16 passes through a beam splitter mirror 18 which may be a turning mirror for aiming the system toward the eye and which may be part of a tracking system which tracks movements of the eye. The mirror 18 may also be used for aiming a surgical laser 20 which may be included in the system, as further discussed below and as shown, for example, in copending application Ser. No. 37,315 referenced above. The illuminating beam 16 passes generally along the axis 14. The illuminating beam 16 passes through an objective lens 22 of the system, by which it is focussed onto the eye 12.

As shown in the drawing, the returning, reflected light from the eye travels along the reflected light axis 14, through the objective lens 22 and is reflected off the mirror 18. With a proper coating on the mirror 18, i.e. a standard high-reflection coating on the side facing the eye (and an anti-reflection coating or no coating on the opposite side), virtually 100% of the reflected light beam 14 will be passed along a continuing, folded optical axis 24 of the system.

FIG. 1 demonstrates the principle of the invention whereby a series of separate spectral components of the reflected light beam 24 may be divided off from the beam 24 and used for different, separate diagnostic purposes. For example, some of the diagnostic uses of different components of the beam can be a corneoscope, an endothelial cell counter, an intraocular pressure monitor, a fluid velocimeter, a spectrometer, a fundus camera or a topographic imaging device such as shown in copending application Ser. No. 456,109, filed Dec. 22, 1989 and assigned to the same assignee as the present invention.

In the example illustrated in FIG. 1, a first coated beam splitter mirror 26 reflects a first spectral division 28 of the reflected light from the eye to a zoom video camera 30 which may be used for imaging features of the eye, and this may include microscopic imaging. A second coated beam splitter mirror 32 may reflect a second spectral division 34 of the reflected light beam into a first ophthalmic diagnostic device 36, which may be, for example, any of the diagnostic devices outlined above. A third coated beam splitter mirror 38 divides out a third spectral division 40 of the reflected light for use in a second diagnostic device 42, which again may be one of the devices outlined above.

FIG. 1 also shows that fourth and fifth coated beam splitter mirrors 44 and 50 may divide out respective spectral divisions 46 and 52 of the beam, for use in further diagnostic or surgery supporting implements 48 and 54. The implement 48 may be a motion recognition detector, which may be used in support of ophthalmic laser surgery using the laser 20 shown in the drawing. The final beam splitter 50 thus allows a surgical laser beam 56 to pass through and to travel along the optical axis 24 toward the eye, to be steered by the turning mirror 18 in response to detection of eye motion during the surgical procedure.

FIG. 2 is a view similar to FIG. 1, but showing another, simpler arrangement still within the principles of the present invention. In FIG. 2 the reflected light beam 14, 24 from the eye 12, reflected by a folding mirror 18, is spectrally divided by only two coated beam splitters 60 and 66. The beam splitter 60 splits out a spectral portion 62 of the reflected light and directed to a first ophthalmic diagnostic device 64. This device can be any of the diagnostic devices outlined above, or, for example, a zoom video camera for imaging portions of the eye. The beam splitter 66 divides out a spectral portion 68 of the reflected light beam and directs it to another ophthalmic diagnostic device 70, which again may be any of the implements discussed above.

In this embodiment, the beam splitter 66 passes the remainder 72 of the reflected light beam 24 to another diagnostic device 74, illustrated as another form of detector for ocular diagnostics. The remainder portion of the light 72 contains all spectral portions which have not been divided out into the spectral divisions 62 and 68. As noted in application Ser. No. 456,109 referenced above, once this multiplicity of devices can operate with reflections arising instantaneously from the same target, new processes which take advantage of this simultaneity become feasible.

FIGS. 3 and 4 illustrate distributions of light according to wavelength—that is, intensity versus wavelength. FIG. 3 shows generally a typical Gaussian distribution as occurs with many examples of ordinary white light. Typically the visible light bands of highest intensity, indicated at 80 and 82 in FIG. 3, are the bands 450 nm to 600 nm, and 600 nm to 750 nm, respectively. These generally represent blue-green and red colors of visible light, respectively. Light in a shorter wavelength range 84, such as 400 nm to 450 nm band, is of slightly lower intensity. A band 86 of still lower wavelengths, such as 300 nm to 400 nm, is considerably lower in intensity, particularly at the lower reaches of the band, as illustrated. This is the ultraviolet end of the spectrum, where most of the wavelength band will be too low in intensity for many diagnostic purposes, given that the peak light intensity must be held to a predetermined limit, such as for ophthalmic diagnostics.

Several additional wavelength bands 88 and 90 illustrated in the Gaussian distribution curve of FIG. 3 are in the infrared range and beyond. As illustrated, portions of the band 88 and normally all of the band 90 will be too low in intensity to be usable for diagnostic purposes such as discussed above. These wavelength ranges may be from about 800 nm to 1200 nm, and from 1200 nm to the effective upper end of the wavelength spectrum. Further subdivisions of the spectral range are possible, if needed, to accommodate a greater number of separate function, co-axial devices.

It can be seen that if the white light illustrated by the distribution shown in FIG. 3 were used for purposes such as a number of diagnostic and imaging and other optical detecting and ophthalmic surgery supporting purposes such as illustrated in FIGS. 1 and 2, without any spectral division of the reflected light beam, each successive beam splitter in the path will reduce the intensity of the remaining light transmitted through the beam splitter. The amount of available light for the various diagnostic and imaging devices is thus determined only by the peak intensity of the reflected light beam. This peak intensity is divided up among the numerous diagnostic and imaging devices, which compete for available light, some requiring considerably more intensity than others. With a considerable number of such devices such as the number shown in FIG. 1, it is often virtually impossible to support all of the devices with the available level of reflected light. The source light beam sent toward the eye (or an industrial workpiece or other element) by the illuminator A or the illuminator B is limited, as discussed above.

Thus, with the present invention, a series of diagnostic devices such as shown in FIG. 1 can be supported, each having adequate light intensity for the particular requirements of the device. As an example, FIG. 3 shows the Gaussian-distributed light spectrum in six different bands. Five of these six separate bands can be selected for the particular requirements of the five implements shown in FIG. 1. Certain devices will be better able to use an ultraviolet signal, and the band 86 can be separated out by the appropriate coated beam splitter and sent to that detector. Certain detectors may not require as high an intensity as others, and to those can be directed the beam spectral divisions 86 or 88. In this way, without increasing the peak intensity of the light directed toward the eye, each detector implement can be sent an adequate intensity of light for the purpose required. The available reflected light is "horizontally divided" in a sense as viewed in FIG. 3, with the different bands having generally similar intensities. This is opposed to the "vertical division" of the light which results from a simple successive splitting of a reflected white light signal, reducing the remaining intensity at each successive splitter.

FIG. 4 is graph diagram showing an enhanced light distribution curve 92 which may be produced and used in accordance with the invention. The flat peak intensity distribution shown in FIG. 4 is particularly advantageous for use in accordance with the principles of the present invention. With this wavelength/intensity distribution, far more wave length bands are usable for the diagnostic, imaging, etc. purposes discussed above, with all bands being at substantially the same intensity.

To produce source light with the spectral distribution generally as shown in FIG. 4, white light can be enhanced at both ends of the spectrum, that is, additional ultraviolet light can be added at the one end, and additional infrared light at the other end. The enhancement preferably is accomplished such that the more extreme and weaker-intensity ranges are bolstered to the greatest degree, so as to produce as wide flat-topped peak intensity curve as possible. Thus, as shown in FIG. 4, the enhancement may take place from about 450 or 500 nm through the ultraviolet and somewhat into the visible violet range; and at the upper extreme of wavelengths, through the infrared range up to about 1200 nm, and perhaps including some or all of the visible red range. Such enhancement can be accomplished, for example, by the use of filters with additional white light added to a white light source of the illuminator, or by adding in light from specific sources, such as generators of bands of ultraviolet and infrared radiation.

Selective coatings which can be used on the beam splitters 26, 32, 38, 44, 50, 60 and 66 are available from Newport Research Corporation. See "Newport Catalog", of Newport Research Corporation, currently published, for example page N-105. See also color separation (dichroic) filters listed in catalog of Optical Coating Laboratory, Inc., Technical Products Division, Box 1599, Santa Rosa, Calif. 95402. Such selective coating technology is well within the knowledge of the art.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

We claim:

1. A method for ophthalmic diagnosis including analysis of reflected light by a plurality of different sensors receiving light from a patient's eye, comprising, sending toward the eye an illuminating light beam from a light source, axially through an optical path, positioning on the optical path, in the path of the illuminating light beam, a plurality of successive beam splitters between the source and the eye, each beam splitter having means for transmitting substantially al of the illuminating light beam toward the eye along the optical path, using optical means, returning light reflected from optical surfaces in the eye back coaxially along the optical path, toward the plurality of successive beam splitters, reflecting off the optical path substantially all light within a first preselected wavelength range, using first coating means on a first beam splitter in the path of the reflected light, and transmitting substantially all of the remaining wavelengths of the reflected light through said first coating means on the first beam splitter, reflecting off the optical path substantially all of the reflected within a second preselected wavelength range using a second coating means on a successive beam splitter of the plurality of beam splitters in the path of reflected light, and transmitting substantially all of the remaining wavelengths of the reflected light through said second coating means on the successive beam splitter, reflecting off the optical path substantially al remaining light using a final coating means on a final reflecting beam splitter, and receiving reflected light in a plurality of detecting optical devices each positioned to receive reflected light from one of the beam splitters, whereby a substantially greater portion of the spectrum of light in the reflected light from the eye is used for diagnostic purposes in the detecting optical devices, enabling the intensity of the illuminating light beam to be minimized and retained within a range of intensity tolerable to the patient.

2. In an optical diagnostic system for ophthalmic analysis in real time using a plurality of sensors receiving reflected light from a patient's eye for diagnostic purposes, a method for illuminating the eye with light of minimal intensity comfortable to the patient while providing adequate reflected light to the plurality of sensors for analysis, comprising, sending toward the eye an illuminating light beam from a light source, the illuminating light beam being within a range of intensity comfortable to the patient, positioning at least one beam splitter in the path of reflected light from the eye, so as to receive light from the illuminating light beam as reflected from optical surfaces in the eye back toward said one beam splitter, providing a first coating means on a first beam splitter in the path of the reflected light, and, using the first coating means, reflecting off the path substantially all light within a first preselected wavelength range, the first coating means transmitting substantially all of the remaining wavelengths of the reflected light, and positioning a plurality of detecting optical devices each to receive a portion of the reflected light from the eye, as divided by at least said one beam splitter, whereby a substantially greater portion of the spectrum of light in the reflected light from the eye is used for diagnostic purposes in the detecting optical devices than would otherwise be available in the absence of spectral division of the reflected light, thereby enabling the intensity of the illuminating light beam to be minimized.

3. The method of claim 2, wherein a plurality of successive beam splitters are positioned in the path of reflected light from the eye, and including providing second coating means on a successive beam splitter of the plurality of beam splitters in the path of the reflected light, to reflect off the path substantially all of the reflected light within a second preselected wavelength range, and transmitting with said successive beam splitter substantially all of the remaining wavelengths of the reflected light, and the plurality of detecting optical devices including at least three detecting devices, each receiving a different spectral portion of the reflected light from the eye.

* * * * *